United States Patent [19]

Gazzi et al.

[11] Patent Number: 4,561,869
[45] Date of Patent: Dec. 31, 1985

[54] CRYOGENIC PROCESS FOR THE SELECTIVE REMOVAL OF ACID GASES FROM GAS MIXTURES BY MEANS OF A SOLVENT

[75] Inventors: Luigi Gazzi; Roberto D'Ambra, both of Milan; Roberto Di Cintio; Carlo Rescalli, both of S.Donato Milanese; Alessandro Vetere, Milan, all of Italy

[73] Assignee: Snamprogetti, S.p.A., Milan, Italy

[21] Appl. No.: 565,454

[22] Filed: Dec. 27, 1983

[30] Foreign Application Priority Data

Jan. 19, 1983 [IT] Italy ............... 19176 A/83

[51] Int. Cl.[4] .............................................. F25J 3/02
[52] U.S. Cl. .......................................... 62/17; 55/68; 55/70; 62/20
[58] Field of Search .............. 62/17, 20; 55/68, 73; 48/196 R; 208/189, 207, 208 R, 236, 347, 350, 351, 354, 355

[56] References Cited

U.S. PATENT DOCUMENTS 4,097,250  6/1978  Pagani et al.
4,305,733 12/1981  Scholz et al. .................. 62/17

*Primary Examiner*—Frank Sever
*Attorney, Agent, or Firm*—Morgan, Finnegan et al.

[57] ABSTRACT

A cryogenic process for removing acid gases from natural or synthesis gases, comprising the following stages:
(a) feeding the natural or synthesis gas to a first absorption column in order to absorb the $H_2S$;
(b) cooling the substantially $H_2S$-free gas to condense part of the $CO_2$ contained in said gas;
(c) feeding the cooled and partly condensed gas to a second absorption column in order to reduce the $CO_2$ content to the required value;
(d) regenerating the solvent or solvents used in the acid gas absorption, the solvent or solvents used being chosen from esters, alcohols or ethers, of low molecular weight.

51 Claims, 2 Drawing Figures

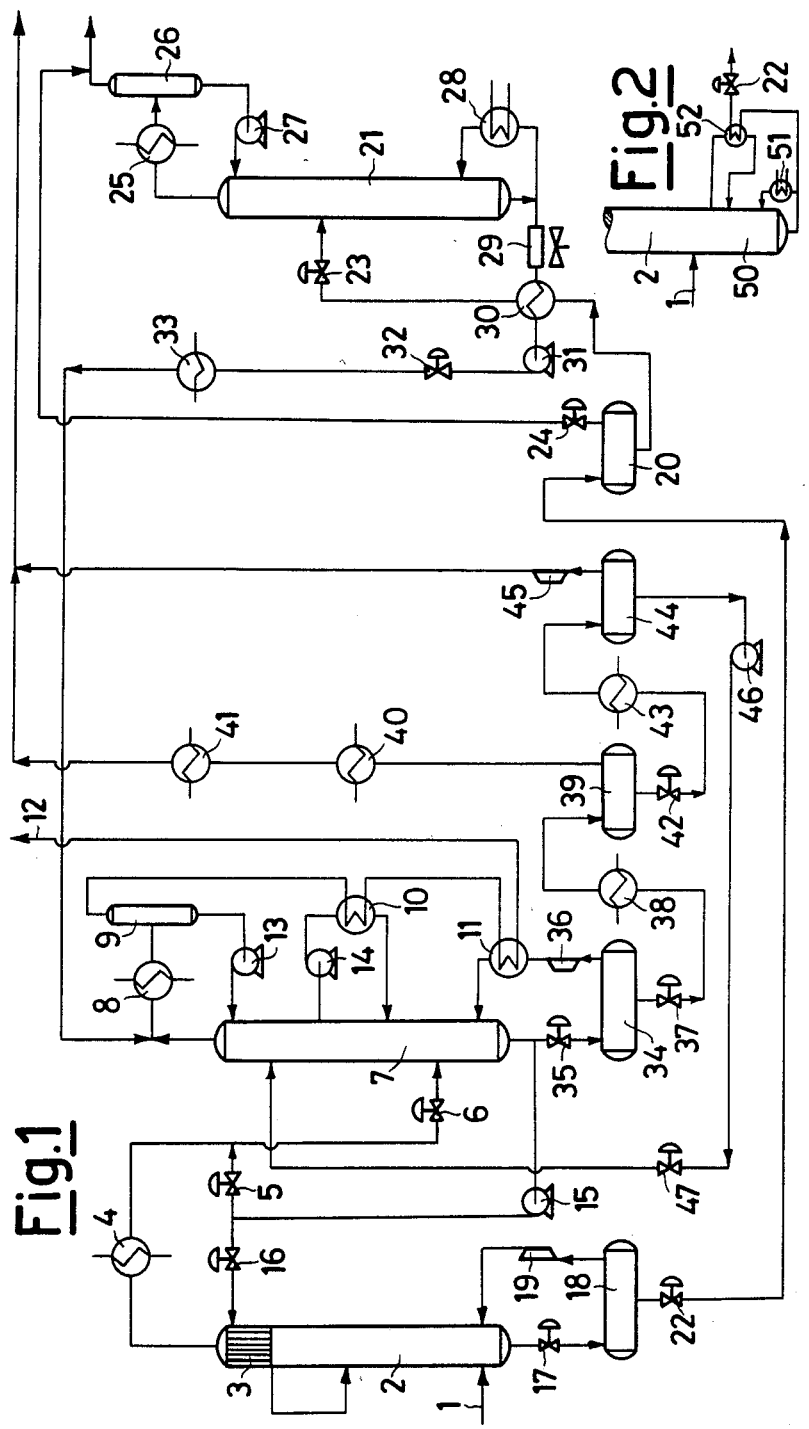

CRYOGENIC PROCESS FOR THE SELECTIVE REMOVAL OF ACID GASES FROM GAS MIXTURES BY MEANS OF A SOLVENT

This invention relates to a process for removing acid gases such as hydrogen sulphide and carbon dioxide from gas mixtures which contain them, which is particularly suitable for treating gaseous mixtures having even very high acid gas contents.

The process of the known art for solving this problem are technically suitable for treating games which when in their crude state contain only relatively small percentages of acid gases.

This is because they were developed during a period in which energy costs were relatively low, and thus only natural gases having low quantities of such components were exploited.

Such processes of the known art can also be used for treating gases of high acid component content, but the economical consequences and in the limit also the technical consequences are unacceptable.

This is because such processes are based essentially on absorption by means of selective solvents which retain the acid components and thus leave the gas purified.

The treatment cost is therefore to a good approximation proportional to the solvent quantity used as a proportion of the gas quantity to be treated. This solvent quantity increases with the constant of acid components.

The purified gas must thus bear the treatment cost. It is therefore apparent that the cost of the treatment according to the known art rises in an unacceptable manner as the acid gas content increases.

In the current energy situation, the use of the available resources must be optimised.

For the exploitation of gas fields of high acid gas content or for purifying synthesis gases produced from fuel oil or coal there is therefore a need for processes suitable for gases of high and very high acid component content able to provide products within a very tight specification.

The treatment of such gases requires the use of mixed cryogenic and solvent methods so as to combine the advantages of the two technologies, in order to obtain good gas purification at acceptable cost. The present invention applicant has already patented a process of this type in U.S. Pat. No. 4,097,250 of 27.6.1979. This patent describes the purification of a crude gas containing more than 70% of acid gases by the combined use of low-temperatue distillation and solvent absorption. The described solvents are dimethyletherpolyethylene glycol and propylene carbonate.

A new purification process has now been discovered, which is particularly suitable for treating gases of high acid gas content, and which uses a class of selective solvents particularly suitable for purification in a cryogenic cycle.

The subject matter of the present invention is the use of such solvents in the treatment cycle described hereinafter. The solvents of the process according to the invention are substantially low molecular weight esters, alcohols and ethers of the following classes:

Alcohol esters of general formula $R_1COOR_2$ where $R_1$ and $R_2$ indicate alkly groups of 1 to 4 carbon atoms, which can be the same or different, in which one or more hydrogen atoms an be substituted by alcohol groups, such as methyl formate, methyl acetate, ethyl acetate or monoethylene glycol acetate.

Glycol esters of general formula

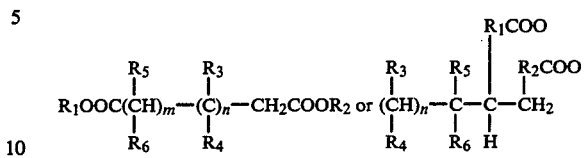

where $R_1$ and $R_2$, which can be the same different, indicate alkyl groups of 1 to 3 carbon atoms, $R_3$, $R_4$, $R_5$, $R_6$, which can be the same or different, indicate either alkyl groups of 1 to 3 carbon atoms or hydrogen atoms, and m and n are whole numbers which can assume the value 0 or 1, examples being 1,3-propanediol diacetate, 2,2-dimethyl-1,3-propanediol diacetate, 1,2-propanediol diacetate and monoethylene glycol diacetate.

Cyclic esters (lactones) of formula

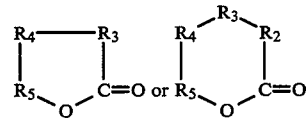

in which $R_2$, $R_3$, $R_4$, $R_5$, which can be the same or different, are alkylene groups in which one or more hydrogen atoms can also be substituted by alklyl, alcohol or ether groups, examples being butyrolactone and caprolactone.

Alcohols of general formula

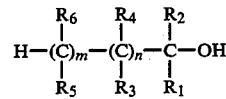

in which $R_1$, $R_2$, $R_3$, $R_4$, $R_5$ and $R_6$, which can be the same or different. are either alkly groups of 1 to 3 carbon atoms or hydroxyl groups or hydrogen atoms, and m and n are whole numbers which can assume the value 0 or 1, examples being monoethylene glycol, diethylene gylcol, 1,2-propanediol, 1,4-butanediol, methanol, ethanol, propanol, isopropanol, n-butanol, isobutanol, sec-butanol, tert-butanol and 1,3-propanediol.

Cyclic ethers such as

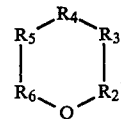

in which $R_2$, $R_3$, $R_5$, $R_6$, which can be the same or different, are alkylene groups in which the hydrogen can also be substituted by alkyl or methoxy groups, $R_3$ can be an oxygen atom or an alkylene group in which the hydrogen can also be substituted by alkyl or methoxy groups, $R_4$ can be as $R_3$, or can be lacking in the case of a five atom ring, examples being tetrahydrofuran, methyl tetrahydrofuran, tetrahydropyran, 1,3-dioxolane, 2-methoxy-1,3-dioxolane and 1,4-dioxane.

Ethers of general formula

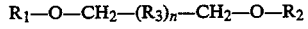

where $R_1$ indicates an alkyl group of 1 to 4 carbon atoms, $R_2$ indicates hydrogen or an alkyl group of 1 to 4 carbon atoms or a hydrogen atom, $R_3$ is either an alkylene group or ($CH_2$—O—$CH_2$), and n is a whole number which can assume the value 0 or 1, examples being 1,2-dimethoxyethane, 1,2-methoxyethoxyethane, dimethoxydiethylene glycol and monomethoxydiethylene glycol.

Ethers of general formula $R_1$—O—$R_2$, where $R_1$ and $R_2$, which can be the same or different, are alkyl groups of 1 to 4 carbon atoms in which one or more hydrogen atoms can be substituted by alcohol groups, examples being ethyl ether, propyl ether, 1-methoxyethanol, 1-methoxy-2-propanol, 1-methoxy-3-propanol and ethoxyethanol.

Ester-ethers, ie compounds containing both the functions, of formula:

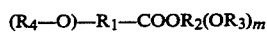

where $R_3$ and $R_4$, which can be the same or different, indicate alkyl groups of 1 to 4 carbon atoms, $R_2$ indicates an alkylene or alkyl group of 1 to 4 carbon atoms, $R_1$ is the same as either $R_2$ or $R_3$, and m and n are whole numbers which can assume the value 0 or 1, examples being 2-methoxyethyl acetate, methylmethoxy acetate and ethylmethoxy acetate.

The aforesaid solvents combine various properties particularly favorable for their use as selective solvents.

In this respect, they have high stability under the conditions in which they are used, high solvent power towards acid gases, high seletively for $H_2S$ compared with $CO_2$ and hydrocarbons, high selectively for $CO_2$ compared with hydrocarbons, low molecular weight and a low melting point. This later characteristic is essential for their application in a cryogenic process.

In the case of natural gas treatment, after low-temperature condensation and before final absorption with solvent, the gas is available at a low temperature substantially less than 0° C.

During final absorption, it is useful to be able to reach a temperature considerably lower than the gas temperature, this being favorable in that it increases the absorbent capacity of the solvent and its selectivity.

Said solvents also have the property of marked selectivity for hydrogen sulphide compared with carbon dioxide, and thus ensure safety with regard to the most dangerous component.

The solvents according to the invention can be used either alone or in mixture, with suitable additions of water and/or of an organic compound of low melting point and/or low viscosity and/or low molecular weight, such as dimethylether, methanol, acetone, toluene, ethanol, propane, butane or pentane, in order to adjust the solvent characteristics as a function of the gas to be treated and its pressure and temperature conditions.

The organic compound can be added in the proportion of between 0.3 and 40% by weight of the resultant mixture, and the water up to a maximum of 10% by weight.

The process according to the invention, which inter alia enables the bleed streams containing the $CO_2$ and $H_2S$ to be obtained substantially separate consists of the following operations:

(a) feeding the natural or synthesis gas to a first absorption column, in order to absorb the $H_2S$;

(b) cooling the substantially $H_2S$-free gas to condense part of the $CO_2$ contained in said gas;

(c) feeding the cooled and partly condensed gas to a second absorption column in order to reduce the $CO_2$ content to the required value;

(d) regenerating the solvent or solvents used in the acid gas absorption.

The substantially $H_2S$-free gas can be cooled in accordance with point (b) in a heat exchanger by vaporising part of the $CO_2$ contained in the $CO_2$-rich solvent at a suitable point of its regeneration. It is preferable for the acid gases which remain uncondensed after cooling under point (b) to not exceed 30 mol% in the gaseous phase, and more preferably to lie between 15 and 30 mol%.

The substantially $H_2S$-free gas can also be cooled in accordance with point (b) inside the second absorption column. Such cooling, which condenses part of the $CO_2$, means that the distillation column used in previous processes can be dispensed with.

The solvent or solvents used for absorbing $H_2S$ in the first absorption column can be initially regenerated by one or more expansion stages (3 at most) from which mainly the useful components co-absorbed in stage a) are recovered, then by a further expansion stage or stages (4 at most) from which mainly $H_2S$ is evolved, then by a distillation column from which mainly $H_2S$ flows as overhead product. The solvents regenerated in this manner are recycled to the second absorption column.

Part of the solvent or solvents used for $CO_2$ absorption in the second absorption column can be regenerated by one or more expansion stages (3 at most), from which mainly the useful components co-absorbed in stage c) are recovered, followed by a further expansion stage or stages (4 at most) from which mainly $CO_2$ is evolved. After regenetration, this part is recycled to the second absorption column. The remainder of the solvent or solvents used for $CO_2$ absorption is fed to the first absorption column.

The useful components evolved during the $H_2S$-rich solvent expansion stages are compressed, cooled and recycled to the first absorption column, whereas those evolved during the $CO_2$-rich solvent expansion stages are compressed, cooled and recycled to the second absorption column.

Alternatively, the useful components of the $H_2S$-rich solvent and of the $CO_2$-rich solvent can be recovered by expanding the two rich solvent streams in an identical number of stages and at the same pressures, then recycling the recovered components to the first absorption column by means of a single compressor.

The expansion stages of the $H_2S$-rich solvents can be carried out through valves or, at least partly, in turbines. The regeneration of the $CO_2$-rich solvent by expansion can be combined with the heating of said solvent in order to favor $CO_2$ removal by vaporisation and to recover cold for use in the process.

The number of expansion stages from which mainly $CO_2$ is evolved can be between 1 and 4, to produce $CO_2$ streams at decreasing pressures, of which one or two can be kept under vacuum, in which case the acid gases which evolve must be recompressed. However, in some cases it is not necessary to go below atmospheric pressure because the final pressure is a function of the temperature attained and of the purification required.

The stream containing mainly $CO_2$ produced at high pressure can be expanded through valves or by turbines down to their required delivery pressure in order to produce work and cold.

The first absorption column operates at a pressure of between 20 and 110 kg/cm$^2$ and at a temperature of between −30° and 40° C.; the second absorption column operates at a pressure of between 20 and 110 kg/cm$^2$ and at a temperature of between −100° and 10° C. Finally the distillation column for solvent regeneration operates at a pressure of between 0.1 and 5 kg/cm$^2$, at an overhead temperature of −60° to 10° C., and at a bottom temperature of between 10° and 200° C. A rectification section can be superposed on the first absorption colum in order to reduce solvent loss in the overhead gas stream from said absorption column, the overhead condenser being cooled by the CO$_2$-rich solvent from the second absorption column before feeding said solvent to the first absorption column.

A further step consists of adding solvent to the natural or synthesis gas leaving the first absorption column before being cooled by heat exchangers or by expansion through valves or turbines in order to prevent CO$_2$ crystallisation.

The solvent of the second absorption column can be withdrawn from an intermediate point of the absorption column, cooled using at least part of the residual cold of the treated gas and/or at least part of the residual cold of the CO$_2$, and fed to the column immediately below its withdrawal point.

The exhausted solvent from the first or second absorption column can be mixed with the natural or synthesis gas and cooled in order to effect preliminary absorption and reduce the load on the absorber.

The regenerated solvent leaving the distillation column can be mixed with the gas leaving the second absorption column and cooled in a heat exchanger before being fed to the second absorption column.

The invention is described hereinafter with reference to the flow diagram of FIG. 1, which represents a preferred embodiment but must not be considered limitative of the invention.

The crude gas reaches the plant through the pipe 1 and is washed in counter-current in the first absorber 2. The absorber comprises a rectification section and a reflex condenser 3 in order to remove a vaporised solvent. The gas is then cooled to condensate a large part of the CO$_2$ in the heat exchanger 4, the solvent is metered-in through the valve 5 in order to prevent CO$_2$ crystallisation, and the gas expanded to its treatment pressure through the valve 6. The expanded gas is washed in counter-current with the solvent in the absorber 7 in order to remove the CO$_2$. The gas leaving the absorber is mixed with completely purified solvent and cooled in the heat exchanger 8, separated from the solvent in 9 and fed for cold recovery to the heat exchangers 10 and 11 and then to the main through the pipe 12. The cooled solvent, separated from the gas in 9, is pumped to the absorber 7 by means of the pump 13. Further solvent, not completely purified, is fed into the absorber at intermediate height. In order to reduce the average absorption temperature, the solvent is extracted from an intermediate plate of the absorber 7, pumped by 14 and cooled against the treated gas in 10.

Part of the CO$_2$-rich solvent leaving the absorber 7 is fed by the pump 15 and valve 16 in order to cool the dephlegmator 3, and then to the absorber 2 in which H$_2$S is absorbed.

The H$_2$S-rich solvent is expanded through the valve 17 and fed to the separator 2. The liquid is expanded into the separator 20 and then into the regeneration column 21 through the valves 22 and 23. The H$_2$S-rich gas which evolves in 20 leaves the plant through the valve 24.

The solvent is stripped of H$_2$S and CO$_2$ in the regenerator 21, which is provided with a condenser 25, reflux accumulator 26, reflux pumps 27 and reboiler 28. This latter is heated by any heat source. The acid gases leaving 26 are added to those from the valve 24. The regenerated solvent is cooled by external cooling means (air or water and/or a suitable refrigeration cycle) in 29 and by the rich solvent in 30, and is then fed by way of the pump 31 and control valve 32 to the cooler 8 after being cooled in the heat exchanger 33.

That part of the CO$_2$-rich solvent not used for H$_2$S absorption is regenerated by expansion.

It is fed through the valve 35 to the separator 34, in which a methane-rich gas is evolved and is recycled to the absorber 7 by means of the compresor 36, after cooling against the treated gas in 11.

The solvent leaving 34 is expanded through the valve 37, heated in 38 and fed to the separator 39, in which CO$_2$ is evolved. It is heated in 40 and 41 and then discharged from the plant.

The solvent leaving 39 is expanded under vacuum through the valve 42, heated in the heat exhaust 43 and then fed to the separator 44. The CO$_2$ is compressed to approximately atmospheric pressure in the compressor 45. The solvent, which still contains a significant quantity of CO$_2$, is fed by way of the pump 46 and control valve 47 to an intermediate level of the absorber 7.

The heat exchanger 38 can be the heat exchanger 4 itself (these however being separated in the figure). In this case, the solvent leaving 34 is heated, thus condensing a large part of the CO$_2$ contained in the crude gas leaving the first absorber.

The heat exchanger 43 can be the heat exchanger 8 itself (again shown separated in the figure).

With the described scheme it is possible to obtain a treated gas containing less than 1 ppm of H$_2$S and less than 10 ppm of CO$_2$. Another possible method for recovering the useful co-absorbed products is shown in FIG. 2. The rich solvent leaving the absorber 2 is directly fed to an exhaustion section 50 situated below the absorber 2. Heat is supplied to the exhaustion section by suitable heating fluids in the bottom reboiler 51 and in the intermediate reboiler 52. This latter cools the column bottom product, which now contains only negligible quantitites of useful compounds. It is expanded through the valve 22 and fed to the separator 20.

The new plant items 50, 51 and 52 replace the plant items 17, 18 and 19 of FIG. 1.

The same device can be used in order to recover the useful compounds co-absorbed in the absorber 7 of FIG. 1. In this case, the plant items to be replaced by the exhaustion section and its accessories are 34, 35, 36 and 11.

We claim:
1. A cryogenic process for the fractional removal of acid gases from natural or synthesis gases containing H$_2$S and CO$_2$, comprising recovering a product which is essentially acid gas free from a feed material having a very high acid gas content of about 50 mole % or more of acid gases by the following steps:
  (a) selectively removing H$_2$S from the natural or synthesis gas in a first absorption column with at least one regeneratable solvent having a high selectivity for H$_2$S;

(b) cooling the substantially H₂S-free gas sufficiently to condense part of the CO₂ contained in said gas so that the acid gases which remain uncondensed do not exceed 30 mole % in the gaseous phase;
(c) selectivity removing CO₂ which remains uncondensed from the cooled and partly condensed gas in a second absorption column with at least one regenerable solvent having a high selectivity for CO₂ in order to produce said essentially acid gas free product; and
(d) regenerating the solvent or solvents used in the CO₂ and H₂S absorption; the solvent or solvents used in the CO₂ and H₂S absorption being selected from the group consisting of low molecular weight esters, alcohols and ethers.

2. The process of claim 1 wherein said solvent comprises an alcohol ester having the formula:

R₁COOR₂, wherein:
R₁ and R₂ represent, independently or simultaneously, C₁-C₄ alkyl in which one or more hydrogen atoms can be substituted by an alcohol group.

3. The process of claim 2, wherein the selective solvent is methylformate, methylacetate, ethylacetate or monoetheleneglycol acetate.

4. The process of claim 1 wherein said solvent comprises a glycol ester having the formula

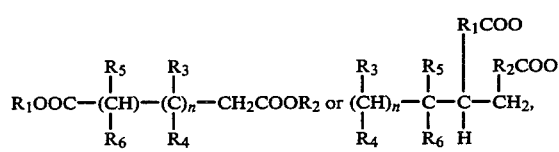

wherein:
R₁ and R₂ represent independently or simultaneously C₁-C₄ alkyl;
R₃, R₄, R₆ represent, independently or simultaneously, C₁-C₃ alkyl or —H; and
m and n are 0 or 1.

5. The process of claim 4, wherein the selective solvent is 1,3-propanediol diacetate, 2,2-dimethyl-1,3-propanediol diacetate, 1,2-propanediol diacetate or monoethyleneglycol diacetate.

6. The process of claim 1 wherein said solvent comprises a cyclic ether having the formula

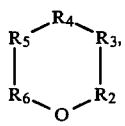

wherein:
R₂, R₅ and R₆ represent, simultaneously or independently, alkylene groups in which one or more of the hydrogens can be substituted by alkyl or methoxy groups;
R₃ represents —O— or an alkylene group in which the hydrogens can be substituted by alkyl or methoxy groups; and
R₄ is equal to R₃ or is absent in the case of a five member ring.

7. The process of claim 6, wherein the selective solvent is tetrahydropyran, 1,3-dioxolane, 1,4-dioxane, tetrahydrofuran, methyltetrahydrofuran, or 2-methoxy-1,3-dioxolane.

8. The process of claim 1, wherein said solvent comprises an ether having the formula:

R₁—O—CH₂—(R₃)ₙ—CH₂—O—R₂, wherein:
R₁ represents C₁-C₄ alkyl;
R₂ represents —H or C₁-C₄ alkyl;
R₃ represents an alkylene group or —CH₂—O—CH₂—; and
n is 0 or 1.

9. The process of claim 8, wherein the selective solvent is 1,2-dimethoxythane, 1,2-methoxyethoxyethane, dimethoxydiethylene glycol or monomethoxydiethylene glycol.

10. The process of claim 1, wherein said solvent comprises an alcohol having the formula

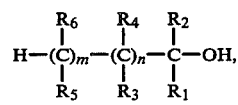

wherein:
R₁, R₂, R₃, R₄, R₅ and R₆ represent, simultaneously or independently, C₁-C₃ alkyl, —OH or —H; and
m and n are 0 or 1.

11. The process of claim 10, wherein the selective solvent is nonethylene glycol, diethylene glycol, 1,2-propanediol, 1,3-propanediol, 1,4-butanediol, methanol, ethanol, propanol, isopropanol, n-butanol, isobutanol, sec-butanol or tert-butanol.

12. The process of claim 1, wherein said solvent comprises a cyclic water (lactone) having the formula

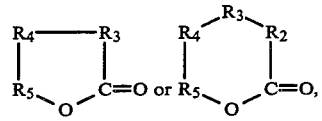

wherein:
R₂, R₃, R₄ and R₅ represent, simultaneously or independently, alkylene groups in which one or more hydrogen atoms can be substituted by alkyl, alcohol or ether groups.

13. The process of claim 12, wherein the selective solvent is butyrolactone or caprolactone.

14. The process of claim 1, wherein said solvent comprises an ether having the formula

R₁—O—R₂, wherein: R₁ and R₂ represent, simultaneously or independently, C₁-C₄ alkyl in which one or more hydrogen can be substituted by an alcohol group.

15. The process of claim 1, wherein the selective solvent is 1-methoxyethanol, 1-methoxy-2-propanol, 1-methoxy-3-propanol, ethoxyethanol, ethyl ether or propyl ether.

16. The process of claim 1, wherein said solvent comprises an ester-ether having the formula (R₄—O)ₙ—R₁—COOR₂(OR₃)m, wherein:

$R_3$ and $R_4$ represent, simultaneously or independently, $C_1$-$C_4$ alkyl:
$R_2$ represents $C_1$-$C_4$ alkylene or alkyl;
$R_1$ represents the same as $R_2$ or $R_3$; and
m and n are 0 or 1.

17. The process of claim 16, wherein the selective solvent is 2-methoxyethyl acetate, methylmethoxy acetate or ethylmethoxy acetate.

18. The process of claim 1, wherein the solvent or solvents used for $H_2S$ absorption in the first absorption column is regenerated initially by one or more expansion stages from which mainly the useful components co-absorbed in stage (a) are recovered, followed by a further expansion stage or stages from which maily $H_2S$ is evolved, followed by treatment in a distillation column wherein the overhead product of said distillation column is mainly $H_2S$, the regenerated solvent or solvents then being recycled to the second absorption column.

19. The process of claim 18, wherein the expansion stages from which mainly the useful components are recovered are from 1 to 3 in number.

20. The process of claims 18 or 19, wherein the useful components which evolve during the $H_2S$-rich solvent expansion stage or stages are compressed, cooled and recycled to the first absorption column.

21. The process of claim 18, wherein the distillation column for solvent regeneration operates at a pressure of between 0.1 and 5 kg/cm$^2$, at an overhead temperature of between $-60°$ and $10°$ C. and at a bottom temperature of between $10°$ and $200°$ C.

22. The process of claim 1 or 18, wherein the regenerated solvent leaving the distillation column is mixed with the gas leaving the second absorption column and cooled in a heat exchanger before being fed to the second absorption column.

23. The process of claim 22, wherein the moisture of regenerated solvent and overhead product gas of the second absorption column is sufficiently cooled to vaporize part of the $CO_2$ contained in the exhausted solvent.

24. The process of claim 1, wherein a part of the solvent or solvents used for $CO_2$ absorption in the second absorption column is regenerated first by one or more expansion stages from which mainly the useful components co-absorbed in stage (c) are recovered, followed by a further expansion stage or stages from which mainly $CO_2$ is evolved, the regenerated part of the solvent then being column, the remaining part of the solvent or solvents used for $CO_2$ absorption being fed to the first absorption column.

25. The process of claim 24, wherein the expansion stages from which mainly the useful components are recovered are from 1 to 3 in number.

26. The process of claim 24 or 25, wherein the useful components evolved from the $CO_2$-rich solvent expansion or expansions are compressed, cooled and recycled to the second absorption column.

27. The process of claim 18, 24, 19 or 25, wherein the useful components are recovered from the $H_2S$-rich solvent and from the $CO_2$-rich solvent by expanding the two acid gas-rich levels solvent streams in the same number of stages at the same pressures and then recycling the recovered useful components to the first absorption column by means of a single compressor.

28. The process of claim 24, wherien the expansion stages from which mainly $CO_2$ is evolved are from 1 to 4 in number of produce $CO_2$ streams at decreasing pressures.

29. The process of claims 24 or 28, wherein the stream or streams containing mainly $CO_2$ produced at high pressure are expanded to their delivery pressure in turbines in order to produce work and refrigeration.

30. The process of claim 24 wherein one or two expansion stages are kept under vacuum.

31. The process of claim 24, wherein the regeneration of the $CO_2$-rich solvent by expansion is supplemented by heating said solvent in order to favor $CO_2$ removal by vaporization and to recover cold for use in the process.

32. The process of claim 18 or 24, wherein the $H_2S$-rich and $CO_2$-rich solvents are expanded through valves or, at least partly, in turbines.

33. The process of claim 24, wherein the second absorption column of stage (c) operates at a pressure of between 20 and 110 kg/cm$^2$ and at a temperature of between $-100°$ and $10°$ C.

34. The process of claim 1, wherein the first absorption column of stage (a) operates at a pressure of between 20 and 110 kg/cm$^2$ and at a temperature of between $-30°$ and $40°$ C.

35. The process of claim 1, wherein a rectification section is superimposed on the first absorption column to reduce solvent loss of the overhead product gas of said absorption column.

36. The process of claim 35, wherein the overhead condenser of the rectification section is cooled by the $CO_2$-rich solvent from the second absorption column before feeding said solvent to the first absorption column.

37. The process of claim 1, wherein solvent is added to the natural or synthesis gas leaving the first absorption column before being cooled by heat exchangers or by expansion through valves or in turbines, in order to prevent $CO_2$ crystallization.

38. The process of claim 1, wherein the solvent used in the second absorption column of stage (c) is withdrawn from an intermediate point of said absorption column, cooled and reintroduced into the column immediately at a point below its withdrawal point.

39. The process of claim 1 or 38, wherein at least part of the intermediate cooling of the solvent is carried out using at least part of the residual cold of the treated gas.

40. The process of claim 1 or 38, wherein at least part of the intermediate cooling of the solvent is carried out using at least part of the residual cold of the $CO_2$.

41. The process of claim 1, wherein the exhausted solvent leaving the first or second absorption columns is mixed with the natural or synthesis gas or is cooled.

42. The process of claim 1, wherein the substantially $H_2S$-free gas is cooled at stage (b) by means of a heat exchanger by a vaporizing part of the $CO_2$ contained in the $CO_2$-rich solvent at an intermedite point of the solvent regeneration.

43. The process of claim 1, wherein cooling at stage (b) is carried out inside the second absorption column.

44. The process of claim 1, wherein the exhausted solvent leaving the first absorption column is fed to an exhaustion section provided with a reboiler in which the useful components are stripped off and fed to the first absorption column.

45. The process of claim 1, wherein part of the exhausted solvent leaving the second absorption column is fed to an exhaustion section provided with a reboiler in which the useful components are stripped off and fed to the second absorption column.

46. The process of claim 44 or 45, wherein the bottom product of the exhaustion section is sub-cooled in an intermediate reboiler of said exhaustion section.

47. The process of claim 1, wherein water and/or an organic compound of low melting point and/or low viscosity and/or low molecular weight are added to the selective solvent or solvents.

48. The process of claim 47, wherein the organic compound is added in the proportion of between 0.3 and 40% by weight of the resultant mixture and the water is added up to a maximum quantity of 10% by weight.

49. The process of claim 47, wherein the organic compound is methanol, dimethylether, ethanol, acetone, propane, butane, pentane, hexane, toluene, or a mixture thereof.

50. The process of claim 1, wherein in said stage (b), the acid gases which remain uncondensed do not exceed 30 mole % in the gaseous phase.

51. The process of claim 50, wherein in said stage (b), the acid gases which remain uncondensed do not exceed 15 mole % in the gaseous phase.

* * * * *

UNITED STATES PATENT AND TRADEMARK OFFICE
CERTIFICATE OF CORRECTION

PATENT NO. : 4,561,869
DATED : December 31, 1985
INVENTOR(S) : Gazzi et al.

It is certified that error appears in the above-identified patent and that said Letters Patent is hereby corrected as shown below:

| Column | Line | |
|---|---|---|
| 7 | 5 | "Selectivity" should be --selectively--; |
| 7 | 41 | "$R_3$, $R_4$, $R_6$" should be --$R_3$, $R_4$, $R_5$ and $R_6$--; |
| 8 | 15 | "1.2- methoxyethoxyethane" should be --1, 2- methoxyethoxyethane--; |
| 8 | 31 | "nonethylene" should be --monoethylene--; |
| 8 | 36 | "water" should be --ester--; |
| 8 | 59 | "Claim 1" should be --claim 14--; |
| 9 | 50 | After "being" insert --recycled to the second absorption--; |

UNITED STATES PATENT AND TRADEMARK OFFICE
CERTIFICATE OF CORRECTION

PATENT NO. : 4,561,869

DATED : December 31, 1985

INVENTOR(S) : Gazzi, et. al.

It is certified that error appears in the above-identified patent and that said Letters Patent is hereby corrected as shown below:

Column 9 line 67 "wherien" should be --wherein--.

Signed and Sealed this

Twenty-fifth Day of May, 1993

Attest:

MICHAEL K. KIRK

Attesting Officer

Acting Commissioner of Patents and Trademarks